United States Patent [19]

Bundy

[11] 4,136,095

[45] Jan. 23, 1979

[54] 5,9α-IMINO- OR 6,9α-IMINOMETHYLENE-9-DEOXY-PGF$_1$ COMPOUNDS

[75] Inventor: Gordon L. Bundy, Portage, Mich.

[73] Assignee: The Upjohn Company, Kalamazoo, Mich.

[21] Appl. No.: 893,585

[22] Filed: Apr. 5, 1978

Related U.S. Application Data

[63] Continuation-in-part of Ser. No. 807,514, Jun. 17, 1977, Pat. No. 4,097,489.

[51] Int. Cl.$^2$ .......................................... C07C 177/00
[52] U.S. Cl. .................................. 546/112; 546/183; 542/429
[58] Field of Search .................. 260/293.54; 542/429

[56] References Cited

U.S. PATENT DOCUMENTS 3,772,312   11/1973   Sturm et al. .................... 260/293.54

*Primary Examiner*—Paul J. Killos
*Attorney, Agent, or Firm*—Robert A. Armitage

[57] ABSTRACT

This invention relates to certain structural and pharmacological analogs of prostacyclin (PGI$_2$) wherein a nitrogen is substituted for the 6,9α-epoxy-oxygen of prostacyclin. These novel nitrogen-containing prostacyclin-type compounds are useful for the pharmacological purposes for which prostacyclin is used, e.g., as antithrombotic agents, antihypertensive agents, antiasthma agents, nasal decongestants, or regulators of tertility and procreation.

53 Claims, No Drawings

5,9α-IMINO- OR 6,9α-IMINOMETHYLENE-9-DEOXY-PGF₁ COMPOUNDS

CROSS REFERENCE TO RELATED APPLICATION

This application is a continuation-in-part of Ser. No. 807,514, filed June 17, 1977, now U.S. Pat. No. 4,097,489, issued June 27, 1978.

The present invention relates to prostacyclin analogs, the essential material constituting a disclosure thereof is incorporated here by reference from Ser. No. 807,514, filed June 17, 1977 now U.S. Pat. No. 4,097,489, issued June 27, 1978.

I claim:

1. A prostacyclin analog of the formula

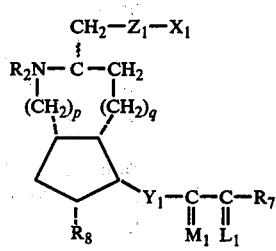

wherein $R_2$ is hydrogen or alkyl of one to 4 carbon atoms, inclusive, or alkylcarbonyl of one to 4 carbon atoms, inclusive;

wherein one of p and q is the integer one and the other is the integer zero;

wherein $Z_1$ is
(1) —(CH₂)$_g$—CH₂—CH₂—,
(2) —(CH₂)$_g$—CH₂—CF₂—, or
(3) trans—(CH₂)$_g$—CH=CH—, wherein g is the integer zero, one, or 2;

wherein $R_8$ is hydrogen, hydroxy, or hydroxymethyl;

wherein $Y_1$ is
(1) trans—CH=CH—
(2) cis—CH=CH—,
(3) —CH₂CH₂—,
(4) trans—CH=C(Hal)—, or
(5) —C≡C— wherein Hal is chloro or bromo;

wherein $M_1$ is

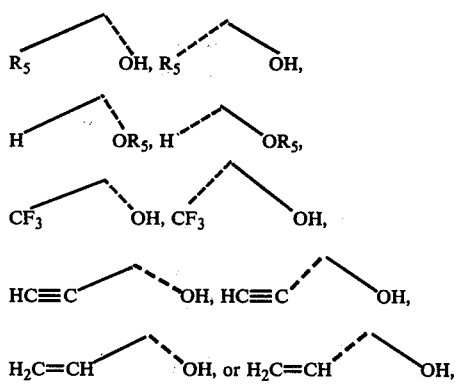

wherein $R_5$ is hydrogen or alkyl with one to 4 carbon atoms, inclusive, wherein $L_1$ is

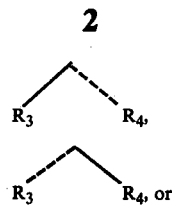

a mixture of

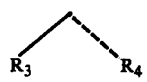

and

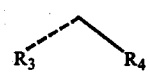

wherein $R_3$ and $R_4$ are hydrogen, methyl, or fluoro, being the same or different, with the proviso that one of $R_3$ and $R_4$ is fluoro only when the other is hydrogen or fluoro;

wherein $X_1$ is
(1) —COOR₁ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

 (a)

 (b)

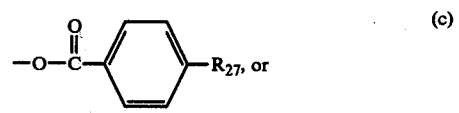 (c)

 (d)

wherein $R_{26}$ is methyl, phenyl, acetamidophenyl, benzamidophenyl, or —NH₂; $R_{26}$ is methyl, phenyl, —NH₂, or methoxy; and $R_{27}$ is hydrogen or acetamido, inclusive; or a pharmacologically acceptable cation;

(2) —CH₂OH; or
(3) —COL₄, wherein $L_4$ is
(a) amino of the formula —NR₂LR₂₂, wherein $R_{21}$ and $R_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substitutted with one, 2, or 3 chloro, alkyl of one to 3 carbon atoms, inclusive, hydroxy, inclusive, carboxy, alkoxycarbonyl of one to 4 carbon atoms, inclusive, or nitro;
(vii) carboxyalkyl of one to four carbon atoms, inclusive;
(viii) carbamoylalkyl of one to four carbon atoms, inclusive;

(ix) cyanoalkyl of one to four carbon atoms, inclusive;
(x) acetylalkyl of one to four carbon atoms, inclusive;
(xi) benzoylalkyl of one to four carbon atoms, inclusive;
(xii) benzoylalkyl substituted by one, 2, or 3 chloro, alkyl of one to 3 carbon atoms inclusive; hydroxy, alkoxy of one to 3 carbon atoms, inclusive; carboxy, alkoxycarbonyl of one to 4 carbon atoms, inclusive, or nitro;
(xiii) hydroxyalkyl of one to 4 carbon atoms, inclusive;
(xiv) dihydroxyalkyl of one to 4 carbon atoms; and
(xv) trihydroxyalkyl of one to 4 carbon atoms; with the further proviso that not more than one of $R_{21}$ and $R_{22}$ is other than hydrogen or alkyl;
(b) carbonylamino of the formula $-NR_{23}COR_{21}$, wherein $R_{23}$ is hydrogen or alkyl of one to 4 carbon atoms and $R_{21}$ is as defined above;
(c) sulphonylamino of the formula $-NR_{23}SO_2R_{21}$, wherein $R_{21}$ and $R_{22}$ are as defined above; or
(d) hydrazino of the formula $-NR_{23}R_{24}$, wherein $R_{24}$ is amino of the formula $-NR_2LR_{22}$, as defined above;
wherein $R_7$ is
(1) $-(CH_2)_m-CH_3$,

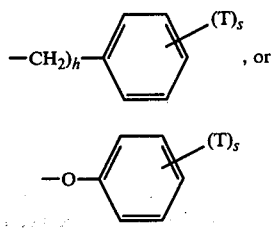

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, or with the proviso that not more than two T's are other than alkyl; and the pharmacologically acceptable acid addition salts thereof when $R_2$ is not alkylcarbonyl and $R_1$ is not a pharmacologically acceptable cation.

2. A prostacyclin analog according to claim 1, wherein $R_8$ is hydroxymethyl.
3. 9,11-Dideoxy-11α-hydroxymethyl-9α,6-iminomethylene-PGF$_1$, a prostacyclin analog according to claim 2.
4. A prostacyclin analog according to claim 1, wherein $R_8$ is hydrogen.
5. 9,11-Dideoxy-9α,6-iminomethylene-PGF$_1$, a prostacyclin analog according to claim 4.
6. A prostacyclin analog according to claim 1, wherein $R_8$ is hydroxy.
7. A prostacyclin analog according to claim 6, wherein p is one.
8. 9-Deoxy-5,9α-imino-PGF$_1$, a prostacyclin analog according to claim 7.
9. A prostacyclin analog according to claim 6, wherein q is one.
10. A prostacyclin analog according to claim 6, wherein $R_2$ is not hydrogen.

11. (6R)-N-methyl-6,9α-iminomethylene-PGF$_1$, a prostacyclin analog according to claim 10.
12. (6R)-N-acetyl-6,9α-iminomethylene-PGF$_1$, a prostacyclin analog according to claim 10.
13. (6S)-N-methyl-6,9α-iminomethylene-PGF$_1$, a prostacyclin analog according to claim 10.
14. (6S)-N-acetyl-6,9α-iminomethylene-PGF$_1$, a prostacyclin analog according to claim 10.
15. A prostacyclin analog according to claim 6, wherein $R_2$ is hydrogen.
16. A prostacyclin analog according to claim 15, wherein $Y_1$ is cis—CH=CH—.
17. 9-Deoxy-9α,6-iminomethylene-cis-13-PGF$_1$, a prostacyclin analog according to claim 16.
18. A prostacyclin analog according to claim 15, wherein $Y_1$ is —C≡C—.
19. 9-Deoxy-9α,6-iminomethylene-13,14-didehydro-PGF$_1$, a prostacyclin analog according to claim 18.
20. A prostacyclin analog according to claim 15, wherein $Y_1$ is trans—CH=C(Hal)—.
21. 9-Deoxy-9α,6-iminomethylene-14-chloro-PGF$_1$, a prostacyclin analog according to claim 20.
22. A prostacyclin analog according to claim 15, wherein $Y_1$ is —CH$_2$CH$_2$—.
23. 9-Deoxy-9α,6-iminomethylene-13,14-dihydro-PGF$_1$, a prostacyclin analog according to claim 22.
24. A prostacyclin analog according to claim 15, wherein $Y_1$ is trans—CH=CH—.
25. A prostacyclin analog according to claim 24, wherein $Z_1$ is —(CH$_2$)$_g$—CH$_2$—CF$_2$.
26. 2,2-Difluoro-9-deoxy-9α,6-iminomethylene-15-methyl-PGF$_1$, a prostacyclin analog according to claim 25.
27. A prostacyclin analog according to claim 24, wherein $Z_1$ is trans—(CH$_2$)$_g$—CH=CH—.
28. Trans-2,3-didehydro-9-deoxy-9α,6-iminomethylene-PGF$_1$, a prostacyclin analog according to claim 27.
29. A prostacyclin analog according to claim 24, wherein $Z_1$ is —(CH$_2$)$_g$—CH$_2$—CH$_2$—.
30. A prostacyclin analog according to claim 29, wherein g is zero.
31. A prostacyclin analog according to claim 30, wherein $R_7$ is $$-(CH_2)_h-\underset{}{\bigcirc}-(T)_s$$

32. 9-Deoxy-9α,6-iminomethylene-17-phenyl-18,19,20-trinor-PGF$_1$, a prostacyclin analog according to claim 31.
33. A prostacyclin analog according to claim 30, wherein $R_7$ is $$-O-\underset{}{\bigcirc}-(T)_s$$

34. 9-Deoxy-9α,6-iminomethylene-16-phenoxy-17,18,19,20-tetranor-PGF$_1$, a prostacyclin analog according to claim 33.
35. A prostacyclin analog according to claim 30, wherein $R_7$ is —(CH$_2$)$_m$—CH$_3$.

36. A prostacyclin analog according to claim 35, wherein m is 3.

37. A prostacyclin analog according to claim 36, wherein $X_1$ is —$COL_4$.

38. 9-Deoxy-9α,6-iminomethylene-$PGF_1$, amide, a prostacyclin analog according to claim 37.

39. A prostacyclin analog according to claim 37, wherein $X_1$ is $CH_2OH$.

40. 2-Decarboxy-2-hydroxymethyl-9-deoxy-9α,6-iminomethylene-$PGF_1$, a prostacyclin analog according to claim 39.

41. A prostacyclin analog according to claim 36, wherein $X_1$ is —$COOR_1$.

42. A prostacyclin analog according to claim 41, wherein $R_5$ is methyl.

43. 9-Deoxy-9α,6-iminomethylene-$PGF_1$, a prostacyclin analog according to claim 42.

44. A prostacyclin analog according to claim 41, wherein $R_5$ is hydrogen.

45. A prostacyclin analog according to claim 44, wherein at least one of $R_3$ and $R_4$ is fluoro.

46. 9-Deoxy-9α,6-iminomethylene-16,16-difluoro-$PGF_1$, a prostacyclin analog according to claim 45.

47. A prostacyclin analog according to claim 44, wherein at least one of $R_3$ or $R_4$ is methyl.

48. 9-Deoxy-9α,6-iminomethylene-16,16-dimethyl-$PGF_1$, a prostacyclin analog according to claim 47.

49. A prostacyclin analog according to claim 48, wherein $R_3$ and $R_4$ are both hydrogen.

50. 9-Deoxy-9α,6-iminomethylene-$PGF_1$, methyl ester, a prostacyclin analog according to claim 49.

51. 9-Deoxy-9α,6-iminomethylene-$PGF_1$, tris(hydroxymethyl)amino methane salt, a prostacyclin analog according to claim 49.

52. 9-Deoxy-9α,6-iminomethylene-$PGF_1$, hydrochloride, a prostacyclin analog according to claim 49.

53. 9-Deoxy-9α,6-iminomethylene-$PGF_1$, a prostacyclin analog according to claim 49.

* * * * *

UNITED STATES PATENT AND TRADEMARK OFFICE
CERTIFICATE OF CORRECTION

PATENT NO. : 4,136,095
DATED : January 23, 1979
INVENTOR(S) : Gordon L. Bundy

It is certified that error appears in the above-identified patent and that said Letters Patent are hereby corrected as shown below:

Column 2, line 54, "$-NR_2LR_{22}$," should read -- $-NR_{21}R_{22}$, --;

Column 3, line 24, "$R_{21}$ and $R_{22}$" should read -- $R_{21}$ and $R_{23}$ --; line 26, "$-NR_2LR_{22}$," should read -- $-NR_{21}R_{22}$, --; lines 30-34, that portion of the formula reading "$-CH_2)_h$" should read -- $(-CH_2)_h$ -- .

*Signed and Sealed this*

*Twenty-fourth* Day of *July 1979*

[SEAL]

*Attest:*

LUTRELLE F. PARKER
*Attesting Officer*   *Acting Commissioner of Patents and Trademarks*

UNITED STATES PATENT OFFICE
CERTIFICATE OF CORRECTION

Patent No. 4,136,095      Dated January 23, 1979

Inventor(s) Gordon L. Bundy

It is certified that error appears in the above-identified patent and that said Letters Patent are hereby corrected as shown below:

Column 5, line 17, should read -- 9-Deoxy-15-methyl-9α,6- --;

Column 6, line 9, should read -- according to claim 44, --.

Signed and Sealed this

Seventeenth Day of June 1980

[SEAL]

Attest:

SIDNEY A. DIAMOND

Attesting Officer  Commissioner of Patents and Trademarks